United States Patent [19]

Photis

[11] 4,209,462

[45] Jun. 24, 1980

[54] METHOD FOR PREPARING ACYL CYANIDES

[75] Inventor: James M. Photis, Ridgefield, Conn.

[73] Assignee: Stauffer Chemical Company, Westport, Conn.

[21] Appl. No.: 970,706

[22] Filed: Dec. 18, 1978

[51] Int. Cl.$^2$ ............................................. C07C 63/06
[52] U.S. Cl. .............................. 260/545 R; 260/347.8; 548/367
[58] Field of Search ........................ 260/545 R, 347.8; 548/367

[56] References Cited

U.S. PATENT DOCUMENTS

| 4,108,875 | 8/1978 | Klenk et al. ..................... 260/545 R |
| 4,113,773 | 9/1978 | Klenk et al. ..................... 260/545 R |

FOREIGN PATENT DOCUMENTS 2614242  10/1977  Fed. Rep. of Germany ........... 260/545

*Primary Examiner*—Howard T. Mars
*Attorney, Agent, or Firm*—William C. Gerstenzang

[57] ABSTRACT

Acyl cyanides are prepared by reacting the corresponding acyl halides with an alkali cyanide in the presence of a catalyst selected from the group consisting of cuprous oxide, elemental copper, and mixtures thereof.

14 Claims, No Drawings

METHOD FOR PREPARING ACYL CYANIDES

BACKGROUND OF THE INVENTION

The present invention relates to a method for the preparation of acyl cyanides. More particularly, the present invention relates to a method for the preparation of acyl cyanides which does not require the use of a copper salt catalyst.

Acyl cyanides are important intermediate products from which other important products, such as herbicides and photoinitiators, can be prepared. The heretofore available methods for their preparation have been limited in number and are generally characterized by the use of HCN or NaCN with a copper (I) salt as catalyst.

Thus, for example, it is well-known in the art to prepare benzoyl cyanide by reacting over-stoichiometric amounts of cuprous cyanide with benzoyl chloride at temperatures up to about 80° C. in acetonitrile or n-butyronitrile; or at temperatures ranging from about 220° C. to about 230° C. in the absence of a solvent.

U.S. Pat. No. 4,113,773 discloses a method for the preparation of benzoyl cyanide wherein a reaction mixture is formed of benzoyl chloride, an alkali cyanide, a carboxylic acid nitrile and a copper (I) salt; and is reacted at a temperature ranging from about 50° C. to about 160° C.

German Offenlegungsschrift No. 2,614,242 discloses a method for preparing acyl cyanides wherein an acyl halide is reacted with an alkali cyanide or hydrocyanic acid in the presence of a heavy metallic cyanide as catalyst.

The heavy metallic cyanide generally used is cuprous cyanide, although zinc cyanide is also mentioned.

The cuprous cyanide employed in these prior art methods is difficult to obtain and often is air oxidized, on storage, to the relatively inactive copper (II) state.

Therefore, a need exists for a new method for the preparation of acyl cyanides in which the catalyst employed is readily available and retains its activity during storage.

It is an object of the present invention to provide a method for the preparation of acyl cyanides wherein the material used as catalyst is readily available and stable.

SUMMARY OF THE INVENTION

It has now been found that acyl cyanides can be prepared by reacting corresponding acyl halides with alkali cyanides in the presence of a catalyst selected from the group consisting of cuprous oxide and elemental copper; both of which are readily available and retain their catalytic activity over prolonged periods of storage.

DETAILED DESCRIPTION OF THE INVENTION

In accordance with the present invention, there is provided a method for preparing acyl cyanides represented by the structural formula:

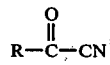

wherein R represents an alkyl group having from 1 to about 8 carbon atoms, cycloalkyl having from 3 to about 12 carbon atoms, optionally substituted aryl or a 5 to 6-membered heterocyclic radical which can optionally be fused to a benzene ring; which comprises reacting an acyl halide represented by the structural formula:

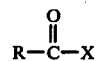

wherein R has the aforedescribed meaning and X represents a halogen selected from the group consisting of fluorine, chlorine, bromine and iodine with an alkali cyanide in the presence of a catalyst selected from the group consisting of cuprous oxide, elemental copper, and mixtures thereof.

As used herein, the term "a 5 or 6-membered heterocyclic radical" means a heterocyclic radical of 5 to 6 members which can contain 1 to 3 hereto atoms such as oxygen, sulfur and/or nitrogen. Included within this definition are radicals such as furanoyl and the like.

As used herein, the term "optionally substituted aryl" means an aryl radical which is unsubstituted or substituted with from 1 to 5 substituents which can be halogen, alkyl, aryl, alkoxy, aryloxy, and the like, it being understood that 1 or more of these substituents can be present on a single aryl radical.

The acyl halides, which can be used in accordance with the method of the present invention include, but are not limited to acetyl chloride, acetyl bromide, propionyl chloride, propionyl bromide, cyclohexanecarboxylic acid chloride (bromide), benzoyl bromide, benzoyl chloride, m-chlorobenzoyl chloride, 3,5-dichlorobenzoyl chloride, naphthalene-1-carboxylic acid chloride, 1-phenyl-5-pyrazolone-3-carboxylic acid chloride, and the like.

An especially preferred acyl halide for use in the practice of the present invention is benzoyl chloride.

Cuprous oxide, elemental copper or mixtures thereof may be used as catalyst in the method of the present invention. It has been observed, however, that under most circumstances cuprous oxide is more convenient to use and is therefore the preferred catalyst. The amount of catalyst used ranges from about 0.005 to about 1.0 moles catalyst per mole of acyl halide. When using cuprous oxide, the preferred catalyst, the amount used preferably ranges from about 0.01 moles cuprous oxide per mole acyl halide to about 0.5 mole cuprous oxide per mole acyl halide.

The alkali cyanides which are reacted with benzoyl chloride in the practice of the present invention include, but are not limited to sodium cyanide, potassium cyanide, and lithium cyanide. The preferred alkali cyanides are sodium cyanide and potassium cyanide, although sodium cyanide is most preferred. The amount of alkali cyanide used in the practice of the present invention is at least the stoichiometric equivalent of the amount of acyl halide used, but is preferably an excess of the equivalent amount. The amount of alkali cyanide used therefore ranges from about 1 to about 3 or more equivalents of the acyl halide used, although preferably it ranges from about 1.05 to about 1.5 equivalents.

The reaction can be conducted either with or without an inert solvent. Suitable solvents are those in which the alkali cyanides are soluble. These solvents include, but are not limited to the aromatic hydrocarbons, such as benzene, toluene, xylene, mesitylene, ethyl benzene, cumeme, p-cumene, t-butyl benzene or 1,3,5-triethyl benzene; aliphatic hydrocarbons such as octane, decane or cyclic hydrocarbons such as decalin, cyclohexane and tetralin; halogenated hydrocarbons such as chlorobenzene, symmetrical tetrachloroethane, carbon tetrachloride, trichloroethylene, trimethylene bromide and ethylene dibromide; ethers such as dioxane, dibutyl ether, dioxolane, ethylene glycol diethyl ether, ethylene glycol dibutyl ether, ethylene glycol and dimethyl ether; esters such as butyl acetate, propyl acetate, amyl acetate, isobutyl acetate, octyl acetate, ethyl propionate, methyl butyrate, ethyl butyrate and methyl valerate; nitrile solvents such as acetonitrile, propionitrile, isobutyronitrile, n-butyronitrile, valeronitrile, capronitrile, caprylonitrile, lauronitrile benzonitrile, o-tolunitrile, p-tolunitrile and m-tolunitrile. Preferred solvents are acetonitrile and butyronitrile, although butyronitrile is particularly preferred.

When conducting the reaction in an inert solvent, the amount of solvent used is not critical. In most applications, however, it will be advantageous to employ from about 10 ml. to about 1000 ml. inert solvent per mole of acyl halide.

The reaction may be conducted at a temperature ranging from about 50° C. to about 300° C. When the reaction is conducted without a solvent, reflux temperatures of the reaction mixture will approximate the boiling point of the acyl halide used, and this will be the most convenient temperature range in which to conduct the reaction under such circumstances. Care must be exercised not to overheat the reaction mixture as product decomposition can result.

It is preferred to conduct the reaction in an inert solvent, because this reduces the temperature necessary for reaction to occur and substantially reduces the probability of decomposing the product by overheating. Thus, for example, when preparing benzoyl cyanide and using butyronitrile as a solvent, the reaction can be conducted at reflux and the temperatures of the reaction mixture can be maintained at about 150° C.

In a particularly preferred embodiment, the present invention comprises a method for preparing benzoyl cyanide which comprises reacting benzoyl chloride with an alkali cyanide in the presence of a catalyst selected from the group consisting of cuprous oxide, elemental copper and mixtures thereof.

The alkali cyanides used in this preferred embodiment are those described earlier, although sodium cyanide is preferred.

When preparing benzoyl cyanide, it is preferable to conduct the reaction at temperatures which do not exceed about 200° C. At temperatures above about 200° C., some product decomposition can occur. Therefore, when preparing benzoyl cyanide in accordance with the method of the present invention, it is preferred to conduct the reaction at a temperature ranging from about 50° C. to about 200° C.

It is particularly preferred to conduct the preparation of benzoyl cyanide in an inert solvent. When so doing, the solvent can be refluxed to maintain the reaction temperature within a desired range. The solvents and amounts in which they can be used are described earlier. Preferred solvents are acetonitrile and butyronitrile, although butyronitrile is particularly preferred, in amounts ranging from about 10 ml. to about 1000 ml. per mole of benzoyl chloride.

It is preferred to conduct the reaction under an inert atmosphere such as nitrogen, argon or the like. In the absence of such an inert atmosphere and at the elevated temperatures at which the reaction is conducted, the reactants and/or products or the reaction can air-oxidize and undergo decomposition.

In order that the present invention be more fully understood, the following examples are given by way of illustration. No specific details or enumerations contained therein should be construed as limitations to the present invention except insofar as they appear in the appended claims. All parts and percentages are by weight unless otherwise specifically designated.

EXAMPLE 1

A one-liter, three-necked, round bottomed flask equipped with a mechanical stirrer, thermometer and reflux condenser was blanketed with nitrogen and 140.5 grams (1.0 mole) benzoyl chloride, 60.0 grams (1.2 moles) sodium cyanide and 4.0 grams cuprous oxide catalyst was added. The mixture was heated, with stirring, to reflux temperature, and maintained at reflux temperature for about 2.5 hours. The temperature of the reaction mixture was not permitted to exceed 200° C.

The reaction mixture was cooled, filtered with the aid of suction and then vacuum distilled to produce 94.4 grams of product (72% yield). The product, which was a white semi-solid material at room temperature, was found to have an infrared spectrum identical to that of a benzoyl cyanide standard.

EXAMPLE 2

Using apparatus and a procedure such as was used in Example 1, 140.5 grams (1.0 mole) of benzoyl chloride, 49.0 grams (1.0 mole) of sodium cyanide and 10.0 grams of Raney copper catalyst were charged to a flask and heated under nitrogen, with stirring, to reflux. During the course of this experiment the temperature of the reaction mixture ranged from 193° to 209° C.

Reaction progress was monitored by infrared spectroscopy. After about 4.5 hours reaction completion was indicated by disappearance of the carbonchloride absorption band (870 cm$^{-1}$).

The reaction mixture was cooled and suction filtered with the aid of a small amount of chloroform to produce a chloroform solution of benzoyl cyanide. Yield of benzoyl cyanide was estimated to be 80% by comparison of the intensity of the benzoyl cyanide band (1680 cm$^{-1}$) with those of the by-product (1710, 1775 cm$^{-1}$) in the infrared spectrum.

EXAMPLE 3

Using apparatus and a procedure such as was used in Example 1, 140.5 grams (1.0 mole) of benzoyl chloride, 55.0 grams (1.1 moles) of sodium cyanide and 20.0 grams of copper filings were charged to a flask and heated under nitrogen, with stirring, to reflux temperature. The reaction mixture was maintained at a temperature ranging from 190° C. to 200° C. for about 4.5 hours. The reaction mixture was then cooled, diluted with 100 ml. toluene and suction filtered. The filtrate was then distilled to produce 75.0 grams (57.3% yield) of benzoyl cyanide having a boiling point of 48° C. at 0.01 mm. Hg. The distilled product became a semi-solid material at room temperature.

EXAMPLE 4

Using apparatus and a procedure such as used in Example 1, 140.5 grams (1.0 mole) of benzoyl chloride, 70.0 grams (1.4 moles) of sodium cyanide, 5.0 grams of cuprous oxide catalyst and 50 ml. of n-butyronitrile solvent were charged to a reaction flask. The mixture was heated under nitrogen, with stirring, to reflux temperature. The mixture was maintained at reflux, with the temperature of the reaction mixture ranging from 148° to 152° C., for two hours.

The reaction mixture was then suction filtered and volatiles were removed using a rotary evaporator. The remaining product, amounting to 138 grams was mixed with 300 ml. of hexane and allowed to stand for about 20 minutes.

The solution was decanted from a small quantity of insoluble black tar and analyzed by infrared spectroscopy from which yield was estimated to be 80%.

The hexane solution of benzoyl cyanide was found to be satisfactory for subsequent transformations.

The object set forth above, among those made apparent from the preceding description are, therefore, effectively attained and, since certain changes may be made in the above method without departure from the scope of the invention, it is intended that all matter contained in the above description shall be interpreted as illustrative and not in a limiting sense.

I claim:

1. A method for preparing acyl cyanides represented by the structural formula:

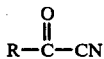

wherein R represents an alkyl group having from 1 to about 8 carbon atoms, cycloalkyl having from 3 to 12 carbon atoms, optionally substituted aryl or a 5 or 6-membered heterocyclic radical which can optionally be fused to a benzene ring; which comprises reacting an acyl halide represented by the structural formula:

wherein R has the aforedescribed meaning and X represents a halogen selected from the group consisting of fluorine, chlorine, bromine and iodine with an alkali cyanide in the presence of a catalyst selected from the group consisting of cuprous oxide, elemental copper and mixtures thereof.

2. The method of claim 1 wherein said reaction is conducted in an inert solvent.

3. The method of claim 2 wherein said reaction is conducted at a temperature ranging from about 50° C. to about 300° C.

4. The method of claim 3 wherein said acyl cyanide is benzoyl cyanide and said acyl halide is benzoyl chloride.

5. The method of claim 4 wherein said reaction is conducted at a temperature ranging from about 50° C. to about 200° C.

6. The method of claim 5 wherein said solvent is selected from the group consisting of acetonitrile and butyronitrile.

7. The method of claim 6 wherein said solvent is butyronitrile.

8. The method of claim 7 wherein said alkali cyanide is sodium cyanide.

9. The method of claim 8 wherein said catalyst is cuprous oxide.

10. A method for preparing benzoyl cyanide which comprises reacting benzoyl chloride with an alkali cyanide in the presence of a catalyst selected from the group consisting of cuprous oxide, elemental copper, and mixtures thereof.

11. The method of claim 10 wherein said reaction is conducted at a temperature ranging from about 50° C. to about 200° C.

12. The method of claim 11 wherein said reaction is conducted in a solvent selected from the group consisting of acetonitrile and butyronitrile.

13. The method of claim 12 wherein said solvent is butyronitrile.

14. The method of claim 13 wherein said alkali cyanide is sodium cyanide.

UNITED STATES PATENT AND TRADEMARK OFFICE
CERTIFICATE OF CORRECTION

PATENT NO. : 4,209,462
DATED : June 24, 1980
INVENTOR(S) : James M. Photis

It is certified that error appears in the above–identified patent and that said Letters Patent are hereby corrected as shown below:

Col. 2, line 18 - "heretoatoms" should be -- heteroatoms --.

Signed and Sealed this

Second Day of September 1980

[SEAL]

Attest:

SIDNEY A. DIAMOND

Attesting Officer

Commissioner of Patents and Trademarks